(12) United States Patent
Mathiasen

(10) Patent No.: US 7,147,623 B2
(45) Date of Patent: Dec. 12, 2006

(54) INFUSION DEVICE WITH NEEDLE SHIELD

(75) Inventor: Orla Mathiasen, Fjenneslev (DK)

(73) Assignee: Unomedical A/S, Lynge (DK)

( * ) Notice: Subject to any disclaimer, the term of this patent is extended or adjusted under 35 U.S.C. 154(b) by 0 days.

(21) Appl. No.: 10/364,242

(22) Filed: Feb. 11, 2003

(65) Prior Publication Data

US 2003/0225374 A1 Dec. 4, 2003

(30) Foreign Application Priority Data

Feb. 12, 2002 (DK) ................ 2002 00208

(51) Int. Cl.
*A61M 5/178* (2006.01)
(52) U.S. Cl. .................. 604/164.08; 128/919
(58) Field of Classification Search ........... 604/110, 604/164.01, 164.07, 164.08, 192, 198, 263; 128/919
See application file for complete search history.

(56) References Cited

U.S. PATENT DOCUMENTS

| | | | |
|---|---|---|---|
| 643,544 A | 2/1900 | Simmons | |
| 1,838,825 A | 12/1931 | Goldstein | |
| 1,991,103 A | 2/1935 | King | |
| 2,047,010 A | 7/1936 | Dickinson | |
| 2,295,849 A | 9/1942 | Kayden | |
| 2,319,731 A | 5/1943 | Garrett | |
| 2,533,731 A | 12/1950 | Gomberg | |
| 2,630,803 A | 3/1953 | Baran | |
| 2,690,529 A | 9/1954 | Lindblad | |
| 2,730,099 A | 1/1956 | Sullivan | |
| 2,839,060 A | 6/1958 | Ormo | |
| 2,936,141 A | 5/1960 | Rapata | |
| 2,952,420 A | 9/1960 | Von Hoorn | |
| 3,055,361 A | 9/1962 | Ballard | |
| 3,107,785 A | 10/1963 | Roehr | |
| 3,074,541 A | 11/1963 | Roehr | |
| 3,154,080 A | 10/1964 | Rowan et al. | |
| 3,317,166 A | 5/1967 | Janssen | |
| 3,545,286 A | 12/1970 | Stenstrom | |
| 3,610,240 A | 10/1971 | Harautuneian | |
| 3,648,999 A | 3/1972 | Bauer | |
| 3,783,996 A | 1/1974 | Gerard et al. | |
| 3,831,729 A | 5/1974 | Howard | |
| 3,814,097 A | 6/1974 | Ganderton et al. | |

(Continued)

FOREIGN PATENT DOCUMENTS

DE 893 296 12/1953

(Continued)

*Primary Examiner*—LoAn H. Thanh
(74) *Attorney, Agent, or Firm*—Brinks Hofer Gilson & Lione

(57) ABSTRACT

The invention relates to a medication infusion set of the type having a flexible cannula adapted for subcutaneous placement, in combination with an insertion, or puncturing, device comprising an insertion needle extending through the cannula and beyond the outer tip thereof, the insertion device further comprising a shield adapted to cover the insertion needle when the latter is withdrawn from the cannula. More specifically, the invention provides a fully integrated shield member having a position in which it covers the cannula and the needle when the insertion device is connected to the housing, a position allowing the cannula to be inserted when the insertion device is connected to the housing, and a position in which the shield covers the needle and the outer tip thereof when the insertion device has been removed from the housing. By this arrangement the need for a separate cover to protect the needle prior to use can be dispensed with.

8 Claims, 6 Drawing Sheets

U.S. PATENT DOCUMENTS

| | | | |
|---|---|---|---|
| 3,840,011 A | 10/1974 | Wright | |
| 3,865,236 A | 2/1975 | Rycroft | |
| 3,942,528 A | 3/1976 | Loeser | |
| 3,986,508 A | 10/1976 | Barrington | |
| 4,014,328 A | 3/1977 | Cluff et al. | |
| 4,022,205 A | 5/1977 | Tenczar | |
| 4,146,113 A | 3/1979 | Gavel | |
| 4,150,798 A | 4/1979 | Aragon | |
| 4,188,950 A | 2/1980 | Wardlaw | |
| 4,201,406 A | 5/1980 | Dennehey et al. | |
| 4,227,528 A | 10/1980 | Wardlaw | |
| 4,267,836 A | 5/1981 | Whitney et al. | |
| 4,306,705 A | 12/1981 | Svenson | |
| 4,315,505 A | 2/1982 | Crandall et al. | |
| 4,334,551 A | 6/1982 | Pfister | |
| D267,199 S | 12/1982 | Koenig | |
| 4,365,630 A | 12/1982 | McFarlane | |
| 4,400,861 A | 8/1983 | Parker | |
| 4,406,042 A | 9/1983 | McPhee | |
| 4,458,344 A | 7/1984 | Coogler | |
| 4,472,024 A | 9/1984 | Konomura et al. | |
| 4,473,369 A | 9/1984 | Lueders et al. | |
| 4,500,312 A | 2/1985 | McFarlane | |
| 4,517,971 A | 5/1985 | Sorbonne | |
| 4,530,695 A | 7/1985 | Phillips et al. | |
| 4,531,686 A | 7/1985 | Shaw | |
| 4,576,846 A | 3/1986 | Noel | |
| 4,606,735 A | 8/1986 | Wilder et al. | |
| 4,610,469 A | 9/1986 | Wolff-Mooij | |
| 4,616,790 A | 10/1986 | Beltran | |
| 4,619,349 A | 10/1986 | Braun | |
| 4,635,683 A | 1/1987 | Nielsen | |
| 4,637,404 A | 1/1987 | Gessman | |
| 4,662,873 A | 5/1987 | Lash et al. | |
| 4,682,702 A | 7/1987 | Gach | |
| 4,713,059 A | 12/1987 | Bickelhaupt et al. | |
| 4,734,092 A | 3/1988 | Millerd | |
| 4,755,173 A | 7/1988 | Konopka et al. | |
| 4,758,020 A | 7/1988 | Boyd | |
| 4,800,629 A | 1/1989 | Ikeda | |
| 4,802,638 A | 2/1989 | Burger et al. | |
| 4,817,603 A | 4/1989 | Turner et al. | |
| RE32,922 E | 5/1989 | Levin et al. | |
| 4,838,871 A | 6/1989 | Luther | |
| 4,840,613 A | 6/1989 | Balbierz | |
| 4,850,974 A | 7/1989 | Bickelhaupt et al. | |
| 4,878,897 A | 11/1989 | Katzin | |
| 4,895,570 A | 1/1990 | Larkin | |
| D306,500 S | 3/1990 | Brahler | |
| 4,913,369 A | 4/1990 | Lia et al. | |
| 4,917,669 A | 4/1990 | Bonaldo | |
| 4,935,010 A | 6/1990 | Cox et al. | |
| 4,950,163 A | 8/1990 | Zimble | |
| 4,950,252 A | 8/1990 | Luther et al. | |
| 4,978,338 A | 12/1990 | Melsky et al. | |
| 4,982,842 A | 1/1991 | Hollister | |
| 4,986,817 A | 1/1991 | Code | |
| 4,994,045 A | 2/1991 | Ranford | 604/198 |
| 5,011,475 A | 4/1991 | Olson | 604/192 |
| 5,024,662 A | 6/1991 | Menes et al. | |
| 5,067,496 A | 11/1991 | Eisele | |
| 5,077,872 A | 1/1992 | Guthammar | |
| 5,083,757 A | 1/1992 | Barsky | |
| 5,098,389 A | 3/1992 | Cappucci | |
| 5,112,313 A | 5/1992 | Sallee | |
| 5,116,319 A | 5/1992 | van den Haak | |
| 5,116,324 A | 5/1992 | Bierley et al. | |
| 5,116,325 A | 5/1992 | Paterson | |
| 5,121,751 A | 6/1992 | Panalletta | |
| 5,134,593 A | 7/1992 | Logan et al. | |
| 5,134,594 A | 7/1992 | Woo | |
| 5,137,524 A | 8/1992 | Lynn et al. | |
| 5,141,496 A | 8/1992 | Dalto et al. | |
| 5,147,319 A | 9/1992 | Ishikawa et al. | |
| 5,147,375 A | 9/1992 | Sullivan et al. | |
| 5,161,681 A | 11/1992 | Kemp et al. | |
| 5,163,915 A | 11/1992 | Holleron | |
| 5,176,662 A | 1/1993 | Bartholomew et al. | |
| 5,188,314 A | 2/1993 | Peters | |
| 5,188,611 A | 2/1993 | Orgain | |
| RE34,223 E | 4/1993 | Bonaldo | |
| 5,222,947 A | 6/1993 | D'Amico | |
| 5,232,454 A | 8/1993 | Hollister | |
| 5,236,143 A | 8/1993 | Dragon | |
| 5,240,199 A | 8/1993 | Peters | |
| 5,248,301 A | 9/1993 | Koenig et al. | |
| 5,256,152 A | 10/1993 | Marks | 604/198 |
| 5,257,980 A | 11/1993 | Van Antwerp et al. | |
| 5,265,822 A | 11/1993 | Shober, Jr. et al. | |
| 5,269,799 A | 12/1993 | Daniel | |
| 5,279,579 A | 1/1994 | D'Amico | |
| 5,279,591 A | 1/1994 | Simon | |
| 5,282,793 A | 2/1994 | Larson | |
| 5,300,030 A | 4/1994 | Crossman et al. | |
| 5,312,359 A | 5/1994 | Wallace | |
| 5,312,369 A | 5/1994 | Arcusin et al. | |
| 5,316,246 A | 5/1994 | Scott et al. | |
| 5,324,302 A | 6/1994 | Crouse | |
| 5,342,319 A | 8/1994 | Watson et al. | |
| 5,342,324 A | 8/1994 | Tucker | |
| 5,343,637 A | 9/1994 | Schindler | |
| 5,350,392 A | 9/1994 | Purcell et al. | |
| 5,354,280 A | 10/1994 | Haber et al. | |
| 5,366,469 A | 11/1994 | Steg et al. | |
| 5,372,592 A | 12/1994 | Gambale | |
| 5,376,082 A | 12/1994 | Phelps | |
| 5,380,067 A | 1/1995 | Turvill et al. | |
| 5,384,174 A | 1/1995 | Ward et al. | |
| 5,387,197 A | 2/1995 | Smith et al. | |
| 5,388,931 A | 2/1995 | Carlson | |
| 5,390,669 A | 2/1995 | Stuart et al. | |
| 5,391,151 A | 2/1995 | Wilmot | |
| 5,403,288 A | 4/1995 | Stanners | |
| 5,405,332 A | 4/1995 | Opalek | |
| 5,429,607 A | 7/1995 | McPhee | |
| 5,429,613 A | 7/1995 | D'Amico | |
| 5,433,307 A | 7/1995 | Jeppe | |
| D362,718 S | 9/1995 | Deily et al. | |
| 5,449,349 A | 9/1995 | Sallee et al. | |
| 5,487,506 A | 1/1996 | Drummond et al. | |
| 5,490,841 A | 2/1996 | Landis | |
| 5,492,313 A | 2/1996 | Pan et al. | |
| 5,505,709 A | 4/1996 | Funderburk et al. | |
| 5,507,730 A | 4/1996 | Haber et al. | 604/187 |
| 5,519,167 A | 5/1996 | Kunimoto et al. | |
| 5,520,654 A | 5/1996 | Wahlberg | |
| 5,522,803 A | 6/1996 | Teissen-Simony | |
| 5,533,974 A | 7/1996 | Gaba | |
| 5,540,709 A | 7/1996 | Ramel | |
| 5,545,143 A | 8/1996 | Fischell | 604/180 |
| 5,545,152 A | 8/1996 | Funderburk et al. | |
| 5,554,130 A | 9/1996 | McDonald et al. | |
| 5,558,650 A | 9/1996 | McPhee | |
| 5,562,636 A | 10/1996 | Utterberg | |
| 5,584,813 A | 12/1996 | Livingston et al. | |
| 5,591,188 A | 1/1997 | Waisman | |
| 5,599,309 A | 2/1997 | Marshall et al. | |
| 5,599,315 A | 2/1997 | McPhee | |
| 5,599,318 A | 2/1997 | Sweeney et al. | |
| 5,628,765 A | 5/1997 | Morita | |
| 5,643,214 A | 7/1997 | Marshall | |
| 5,643,216 A | 7/1997 | White | |
| 5,643,220 A | 7/1997 | Cosme | |
| 5,662,617 A | 9/1997 | Odell et al. | |

| | | | | | | |
|---|---|---|---|---|---|---|
| 5,665,071 A | 9/1997 | Wyrick | | 6,579,267 B1 | 6/2003 | Lynch et al. |
| 5,665,075 A | 9/1997 | Gyure et al. | | 6,582,397 B1 | 6/2003 | Alesi et al. |
| 5,681,323 A | 10/1997 | Arick | | 6,595,962 B1 | 7/2003 | Perthu |
| 5,695,476 A | 12/1997 | Harris ................... 604/198 | | 6,607,509 B1 | 8/2003 | Bobroff et al. |
| 5,704,920 A | 1/1998 | Gyure | | 6,607,511 B1 | 8/2003 | Halseth et al. |
| 5,709,516 A | 1/1998 | Peterson et al. | | 6,629,949 B1 | 10/2003 | Douglas |
| 5,714,225 A | 2/1998 | Hansen et al. | | 6,645,182 B1 | 11/2003 | Szabo |
| 5,741,288 A | 4/1998 | Rife | | 6,685,674 B1 | 2/2004 | Douglas et al. |
| 5,752,923 A | 5/1998 | Terwilliger | | 6,702,779 B1 | 3/2004 | Connelly et al. |
| 5,810,835 A | 9/1998 | Ryan et al. | | 6,726,649 B1 | 4/2004 | Swenson et al. |
| 5,820,598 A | 10/1998 | Gazza et al. | | 6,736,797 B1 | 5/2004 | Larsen et al. |
| D402,538 S | 12/1998 | Wagter et al. | | 6,749,589 B1 | 6/2004 | Douglas et al. |
| 5,843,001 A | 12/1998 | Goldenberg | | 6,790,199 B1 | 9/2004 | Gianakos |
| 5,851,197 A | 12/1998 | Marano et al. | | 6,805,686 B1 | 10/2004 | Fathallah et al. |
| 5,858,001 A | 1/1999 | Tsals et al. | | 6,811,545 B1 | 11/2004 | Vaillancourt |
| 5,865,806 A | 2/1999 | Howell | | 6,814,720 B1 | 11/2004 | Olsen et al. |
| 5,873,540 A | 2/1999 | Hardin | | 6,824,530 B1 * | 11/2004 | Wagner et al. ............... 604/162 |
| 5,899,886 A | 5/1999 | Cosme | | 6,824,531 B1 | 11/2004 | Zecha, Jr. et al. |
| 5,913,846 A | 6/1999 | Szabo | | 6,830,562 B1 | 12/2004 | Mogensen et al. |
| 5,915,640 A | 6/1999 | Wagter et al. | | 6,837,877 B1 | 1/2005 | Zurcher |
| 5,919,167 A | 7/1999 | Mulhauser et al. | | 6,840,922 B1 | 1/2005 | Nielsen et al. |
| 5,925,032 A | 7/1999 | Clements | | 6,880,701 B1 | 4/2005 | Bergeron et al. |
| 5,947,935 A | 9/1999 | Rhinehart et al. | | 6,916,017 B1 | 7/2005 | Noe |
| 5,951,523 A | 9/1999 | Osterlind et al. | | 6,923,791 B1 | 8/2005 | Douglas |
| 5,954,643 A | 9/1999 | VanAntwerp et al. | | 6,926,694 B1 | 8/2005 | Marano-Ford et al. |
| 5,957,892 A * | 9/1999 | Thorne ................... 604/162 | | 6,939,331 B1 | 9/2005 | Ohshima |
| 5,968,011 A | 10/1999 | Larsen et al. | | 6,949,084 B1 | 9/2005 | Marggi et al. |
| 5,975,120 A | 11/1999 | Novosel | | 2001/0004970 A1 | 6/2001 | Hollister et al. |
| 5,980,488 A | 11/1999 | Thorne | | 2001/0016714 A1 | 8/2001 | Bell et al. |
| 5,980,506 A | 11/1999 | Mathiasen | | 2001/0021827 A1 | 9/2001 | Ferguson et al. |
| 5,984,640 A | 11/1999 | Wang | | 2001/0039401 A1 | 11/2001 | Ferguson et al. |
| 5,984,897 A | 11/1999 | Peterson et al. | | 2001/0041875 A1 | 11/2001 | Higuchi et al. |
| 5,992,787 A | 11/1999 | Burke | | 2002/0022855 A1 | 2/2002 | Bobroff et al. |
| D417,733 S | 12/1999 | Howell et al. | | 2005/0101933 A1 | 5/2002 | Marrs et al. |
| 6,017,328 A | 1/2000 | Fischell et al. | | 2002/0068904 A1 | 6/2002 | Pluth et al. |
| D421,119 S | 2/2000 | Musgrave et al. | | 2002/0072720 A1 | 6/2002 | Hague et al. |
| 6,039,629 A | 3/2000 | Mitchell | | 2002/0077599 A1 | 6/2002 | Wojcik |
| 6,042,570 A | 3/2000 | Bell et al. | | 2002/0107489 A1 | 8/2002 | Lee |
| 6,045,533 A | 4/2000 | Kriesel et al. | | 2002/0111581 A1 | 8/2002 | Sasso |
| 6,050,976 A | 4/2000 | Thorne et al. | | 2002/0145073 A1 | 10/2002 | Swanson et al. |
| 6,056,718 A | 5/2000 | Funderburk et al. ........ 604/193 | | 2002/0156424 A1 | 10/2002 | Suzuki et al. |
| 6,074,371 A | 6/2000 | Fischell | | 2002/0156427 A1 | 10/2002 | Suzuki et al. |
| 6,086,008 A | 7/2000 | Gray et al. | | 2002/0161332 A1 | 10/2002 | Ramey |
| 6,086,575 A | 7/2000 | Mejslov | | 2002/0169419 A1 | 11/2002 | Steg |
| 6,090,068 A | 7/2000 | Chanut | | 2002/0173748 A1 | 11/2002 | McConnell et al. |
| 6,093,172 A | 7/2000 | Funderburk et al. | | 2002/0183688 A1 | 12/2002 | Lastovich et al. |
| 6,093,179 A | 7/2000 | O'Hara et al. | | 2002/0189688 A1 | 12/2002 | Roorda |
| 6,099,503 A | 8/2000 | Stardella | | 2002/0193737 A1 | 12/2002 | Popovsky |
| 6,105,218 A | 8/2000 | Reekie | | 2002/0193744 A1 | 12/2002 | Alesi et al. |
| 6,120,482 A | 9/2000 | Szabo | | 2003/0069548 A1 | 4/2003 | Connelly et al. |
| 6,123,690 A | 9/2000 | Mejslov | | 2003/0105430 A1 | 6/2003 | Lavi et al. |
| 6,132,755 A | 10/2000 | Eicher et al. | | 2003/0109829 A1 | 6/2003 | Mogensen et al. |
| 6,183,464 B1 | 2/2001 | Sharp et al. | | 2003/0125669 A1 | 7/2003 | Safabash et al. |
| 6,193,694 B1 | 2/2001 | Bell et al. | | 2003/0125678 A1 | 7/2003 | Swenson et al. |
| 6,219,574 B1 | 4/2001 | Cormier et al. | | 2003/0130619 A1 | 7/2003 | Safabash et al. |
| 6,221,058 B1 | 4/2001 | Kao et al. | | 2003/0139704 A1 | 7/2003 | Lin |
| 6,248,093 B1 | 6/2001 | Moberg | | 2003/0158520 A1 | 8/2003 | Safabash et al. |
| 6,293,925 B1 | 9/2001 | Safabash et al. | | 2003/0176843 A1 | 9/2003 | Wilkinson |
| 6,302,866 B1 | 10/2001 | Marggi | | 2003/0181863 A1 | 9/2003 | Davis et al. |
| 6,319,232 B1 | 11/2001 | Kashmer | | 2003/0181868 A1 | 9/2003 | Swenson |
| 6,322,535 B1 | 11/2001 | Hitchins et al. | | 2003/0181873 A1 | 9/2003 | Swenson |
| 6,322,808 B1 | 11/2001 | Trautman et al. | | 2003/0181874 A1 | 9/2003 | Bressler et al. |
| 6,334,856 B1 | 1/2002 | Allen et al. | | 2003/0187394 A1 | 10/2003 | Wilkinson et al. |
| 6,355,021 B1 * | 3/2002 | Nielsen et al. ............... 604/263 | | 2003/0187395 A1 | 10/2003 | Wilkinson et al. |
| 6,379,335 B1 | 4/2002 | Rigon et al. | | 2003/0199823 A1 | 10/2003 | Bobroff et al. |
| D456,692 S | 5/2002 | Epstein | | 2003/0216686 A1 | 11/2003 | Lynch et al. |
| 6,387,076 B1 | 5/2002 | Landuyt | | 2003/0225373 A1 | 12/2003 | Bobroff et al. |
| 6,488,663 B1 | 12/2002 | Steg | | 2003/0225374 A1 | 12/2003 | Mathiasen |
| 6,517,517 B1 | 2/2003 | Farrugia et al. | | 2003/0229308 A1 | 12/2003 | Tsals et al. |
| 6,520,938 B1 * | 2/2003 | Funderburk et al. ... 604/164.08 | | 2003/0229316 A1 | 12/2003 | Hwang et al. |
| D472,316 S | 3/2003 | Douglas et al. | | 2004/0002682 A1 | 1/2004 | Kovelman et al. |
| D472,630 S | 4/2003 | Douglas et al. | | 2004/0006316 A1 | 1/2004 | Patton |
| 6,572,586 B1 | 6/2003 | Wojcik | | 2004/0026840 A1 | 2/2004 | Eckel et al. |

| | | | | | | |
|---|---|---|---|---|---|---|
| 2004/0044306 A1 | 3/2004 | Lynch et al. | EP | 0 931 560 A1 | 7/1999 | |
| 2004/0049159 A1 | 3/2004 | Barrus et al. | EP | 0 956 879 A1 | 11/1999 | |
| 2004/0068231 A1 | 4/2004 | Blondeau | EP | 1 045 145 A1 | 10/2000 | |
| 2004/0087913 A1 | 5/2004 | Rogers et al. | EP | 1 060 757 A1 | 12/2000 | |
| 2004/0111068 A1 | 6/2004 | Swenson | EP | 1 086 718 A | 3/2001 | |
| 2004/0112781 A1 | 6/2004 | Hofverberg et al. | EP | 1 125 593 A1 | 8/2001 | |
| 2004/0116865 A1 | 6/2004 | Bengtsson | EP | 1 167 765 A2 | 1/2002 | |
| 2004/0138612 A1 | 7/2004 | Shermer et al. | EP | 0 775 501 | 6/2002 | |
| 2004/0138620 A1 | 7/2004 | Douglas et al. | EP | 0 894 216 B1 | 7/2003 | |
| 2004/0143216 A1 | 7/2004 | Douglas et al. | EP | 1 380 315 A1 | 1/2004 | |
| 2004/0143218 A1 | 7/2004 | Das | EP | 0 956 879 A1 | 7/2004 | |
| 2004/0158202 A1 | 8/2004 | Jensen | FR | 576 849 | 8/1924 | |
| 2004/0158207 A1 | 8/2004 | Hunn et al. | FR | 2 611 013 | 8/1988 | |
| 2004/0162518 A1 | 8/2004 | Connelly et al. | FR | 2725902 | 10/1994 | |
| 2004/0171989 A1 | 9/2004 | Horner et al. | FR | 2 733 915 | 11/1996 | |
| 2004/0178098 A1 | 9/2004 | Swenson et al. | FR | 2733915 | 11/1996 | |
| 2004/0186446 A1 | 9/2004 | Ohshima | FR | 2 781 617 A1 | 1/2000 | |
| 2004/0199123 A1 | 10/2004 | Nielsen | FR | 2781617 | 1/2000 | |
| 2004/0204687 A1 | 10/2004 | Mogensen et al. | GB | 478803 | 1/1938 | |
| 2004/0204690 A1 | 10/2004 | Yashiro et al. | GB | 591730 | 3/1946 | |
| 2004/0220528 A1 | 11/2004 | Garcia, Jr. | GB | 906574 | 9/1962 | |
| 2004/0238392 A1 | 12/2004 | Peterson et al. | GB | 1 268 575 | 3/1972 | |
| 2004/0243065 A1 | 12/2004 | McConnell et al. | GB | 1 403 034 | 8/1975 | |
| 2004/0254433 A1 | 12/2004 | Bandis et al. | GB | 2 224 808 A | 5/1990 | |
| 2004/0260235 A1 | 12/2004 | Douglas | GB | 2 270 552 A | 3/1994 | |
| 2004/0260250 A1 | 12/2004 | Harris et al. | JP | 05326062 A | 12/1993 | |
| 2005/0035014 A1 | 2/2005 | Cane | JP | 5326062 A | 12/1993 | |
| 2005/0101932 A1 | 5/2005 | Cote et al. | JP | 7051251 | 11/1995 | |
| 2005/0107743 A1 | 5/2005 | Fangrow, Jr. | JP | 9217584 A | 9/1997 | |
| 2005/0113761 A1 | 5/2005 | Faust et al. | JP | 2000-59877 A | 2/2000 | |
| 2005/0119637 A1 | 6/2005 | Lundgren et al. | JP | 3140740 | 2/2000 | |
| 2005/0124936 A1 | 6/2005 | Mogensen et al. | JP | 2000059877 A | 2/2000 | |
| 2005/0159709 A1 | 7/2005 | Wilkinson | JP | 3140740 B2 | 3/2001 | |
| 2005/0215979 A1 | 9/2005 | Konerup et al. | JP | 2002-028246 | 1/2002 | |
| 2005/0251098 A1 | 11/2005 | Wyss et al. | NL | 1017427 C | 11/2002 | |
| 2005/0277892 A1 | 12/2005 | Chen | WO | WO 87/06474 | 11/1987 | |
| 2005/0283114 A1 | 12/2005 | Bresina et al. | WO | WO 93/03787 | 3/1993 | |
| 2006/0030815 A1 | 2/2006 | Csincsura et al. | WO | WO 93/05840 | 4/1993 | |
| | | | WO | WO 94/20160 | 9/1994 | |
| FOREIGN PATENT DOCUMENTS | | | WO | WO 95/28327 A | 10/1995 | |
| DE | 1 053 541 | 3/1959 | WO | WO 96/35472 A1 | 11/1996 | |
| DE | 26 20 009 A1 | 12/1977 | WO | WO 98/09065 | 3/1998 | |
| DE | 28 03 509 A1 | 8/1978 | WO | WO 98/58693 | 12/1998 | |
| DE | 37 15 965 A | 1/1988 | WO | WO 99/07435 | 2/1999 | |
| DE | 196 31 921 | 3/1997 | WO | WO 99/33504 | 7/1999 | |
| DE | 298 18 311 U1 | 3/1999 | WO | WO 99/36009 | 7/1999 | |
| DE | 19847143 A1 | 1/2000 | WO | WO 99/56802 | 11/1999 | |
| DE | 299 24 406 U1 | 1/2001 | WO | WO 99/61815 | 12/1999 | |
| DE | 101 06 074 A1 | 6/2002 | WO | WO 00/02614 | 1/2000 | |
| DK | 37 22 893 C1 | 6/1988 | WO | WO 00/03757 | * | 1/2000 |
| DK | 38 23 447 | 2/1996 | WO | WO 00/44324 A1 | 8/2000 | |
| DK | 196 10 692 A1 | 9/1997 | WO | WO 01/04507 A1 | 1/2001 | |
| DK | 198 47 143 A1 | 1/2000 | WO | WO 01/30419 A2 | 5/2001 | |
| DK | 100 49 001 A1 | 4/2002 | WO | WO 01/68180 A1 | 9/2001 | |
| EP | 0 188 014 B1 | 10/1985 | WO | WO 01/81785 A1 | 11/2001 | |
| EP | 0 239 244 B1 | 2/1987 | WO | WO 01/93926 A2 | 12/2001 | |
| EP | 0 298 521 B1 | 9/1990 | WO | WO 02/46080 | 6/2002 | |
| EP | 0 184 231 B1 | 1/1992 | WO | WO 02/066854 A1 | 8/2002 | |
| EP | 0 475 857 | 3/1992 | WO | WO 02/094352 | 11/2002 | |
| EP | 0 544 837 | 6/1993 | WO | WO 02/100457 | 12/2002 | |
| EP | 0 633 039 | 7/1994 | WO | WO 02/068014 | 1/2003 | |
| EP | 0 651 662 B1 | 5/1995 | WO | WO 03/015861 A1 | 2/2003 | |
| EP | 0 714 631 B1 | 6/1996 | WO | WO 03/026728 | 4/2003 | |
| EP | 744 183 A2 | 11/1996 | WO | WO 04/030726 A | 4/2004 | |
| EP | 0 747 006 A1 | 12/1996 | WO | WO 04/087240 | 10/2004 | |
| EP | 0 688 232 B1 | 12/1998 | WO | WO 05/004973 | 1/2005 | |
| EP | 0 884 108 A1 | 12/1998 | | | | |
| EP | 0 916 361 A1 | 5/1999 | * cited by examiner | | | |

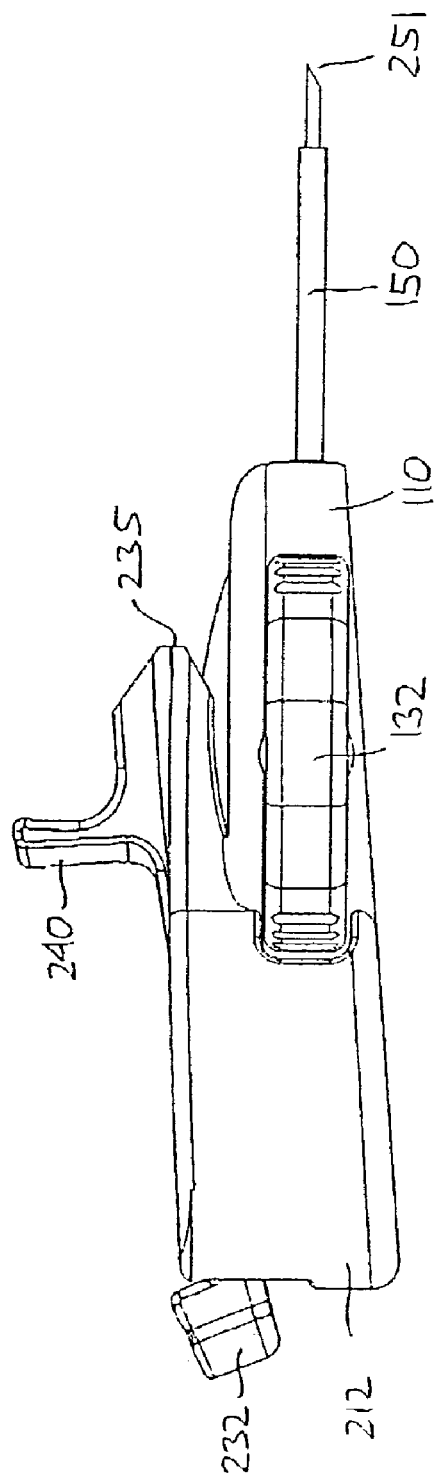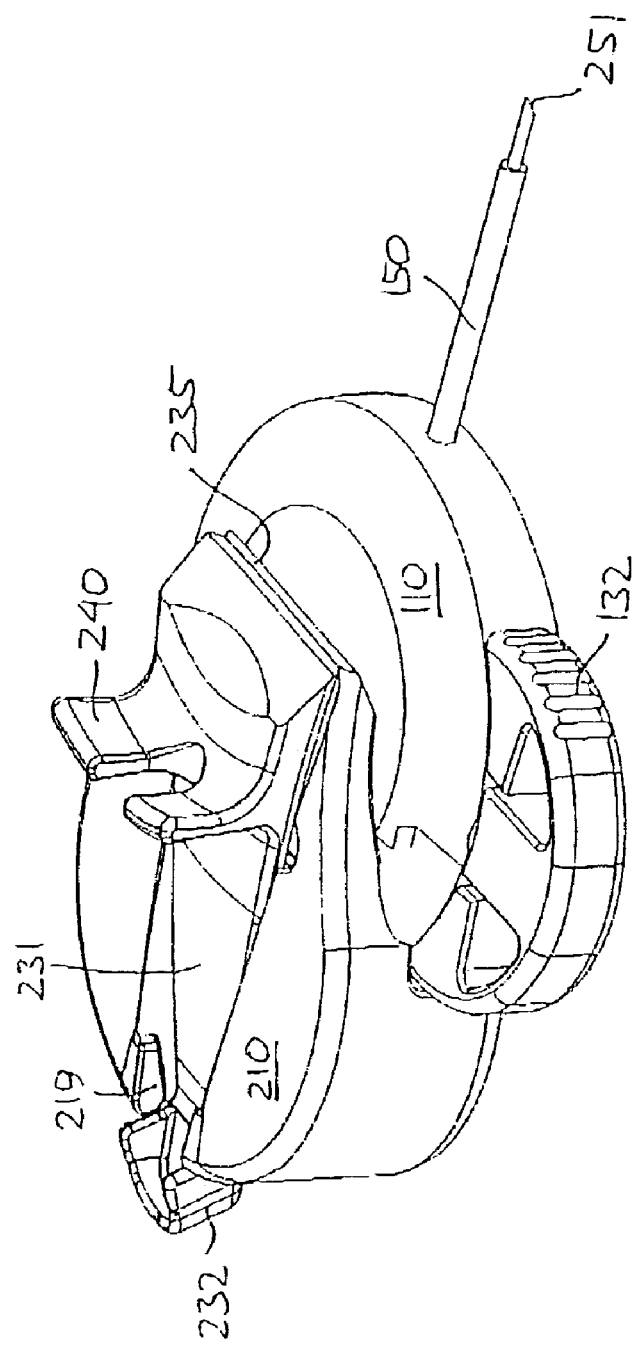

ial application claims priority to Danish Application PA 2002 00208, filed Feb. 12, 2002, the entirety of this reference is incorporated herein.

INFUSION DEVICE WITH NEEDLE SHIELD

This application claims priority to Danish Application PA 2002 00208, filed Feb. 12, 2002, the entirety of this reference is incorporated herein.

FIELD OF THE INVENTION

The invention relates generally to devices for delivering a selected medication or another therapeutic fluid to a patient at a subcutaneous or other infusion site. More particularly, the invention relates to a medication infusion set of the type having a flexible cannula adapted for subcutaneous placement, in combination with an insertion, or puncturing, device comprising an insertion needle extending through the cannula and beyond the outer tip thereof, the insertion device further comprising a shield adapted to cover the insertion needle when the latter is withdrawn from the cannula.

BACKGROUND OF THE INVENTION

Medication injection or infusion sets are generally well known in the art, to include a relatively soft and flexible cannula providing a transcutaneous pathway through which a selected medication or other therapeutic fluid can be administered to a patient at a selected subcutaneous site. In a common form, the soft cannula is carried by a housing initially assembled with an insertion needle extending through the cannula, wherein the insertion needle is manipulated to pierce the patient's skin to place the cannula transcutaneously, followed by withdrawal of the insertion needle to leave the soft cannula in place on the patient. In order to allow the insertion needle to be handled, the needle is normally provided as an insertion device comprising a hub to which the needle is attached.

The selected medication may then be coupled to the cannula, typically by means of a length of infusion tubing connected to a medication source to deliver the medication through the cannula to the patient.

In one configuration, the infusion tubing is connected to the cannula housing corresponding to the opening through which the insertion needle has been withdrawn from the cannula, i.e. the tubing is arranged axially with respect to the general axial orientation of the cannula. An example of this type of infusion device is disclosed in U.S. Pat. No. 6,056,718.

In a second configuration, the infusion tubing is connected to the cannula housing at a location different from the opening through which the insertion needle is inserted into the cannula, this configuration allowing the tubing to be pre-connected to the housing. An example of this type of infusion device is known from WO 00/03757 and U.S. Pat. No. 5,545,143 both disclosing a device in which the cannula and insertion needle are arranged perpendicular to tubing. In order to seal the device, a self-sealing penetratable septum is provided corresponding to the opening through which the insertion needle is withdrawn, this septum also allowing samples to be taken without having to disconnect the tubing.

The use of insertion needles, or needle devices in general, is associated with some disadvantages during use thereof due to the potential danger of exposure to the pointed tip before use as well as after the needle has been withdrawn and before it has been properly discarded. Correspondingly, a large number of needle protection devices have been proposed to provide a remedy to this problem.

A very simple form of protection is the traditional tubular sleeve which normally covers the needle when supplied to the user, for example as shown in U.S. Pat. No. 5,545,143; after use the cover may be used to cover the needle again, however, in most cases the needle and the cover are discarded separately A more elaborate shell-shaped needle guard is disclosed in U.S. Pat. No. 6,056,718, however, basically this guard functions as a simple needle cover to be removed from the insertion device prior to use.

In order to better protect against unintended needle prick, a number of shield devices has been proposed based on the principle that a pivotable shield is mounted corresponding to the front of the device, this allowing the shield to be pivoted away before use of the needle as well as used to cover the needle immediately after use, An example of this type of needle protection device is disclosed in U.S. Pat. No. 5,011,475.

For the above-described type of infusion devices in which an insertion needle is arranged through a cannula, different solutions have been proposed. For example, a recent type of needle protection devices is based upon the principle that a protecting means automatically grips the needle tip as the insertion needle is withdrawn from the infusion device, however, this solution requires a separate cover to protect the needle prior to use, A different approach is known from WO 00/03757 disclosing an infusion device in which an insertion needle hub is provided with a hinged shield member protruding there from, whereby the shield member is adapted to pivot and thereby cover the insertion needle when withdrawn from the infusion device. Also this solution requires a separate cover to protect the needle prior to use.

SUMMARY OF THE INVENTION

Having regard to the above discussion of the prior art, the object of the present invention is to provide an infusion device comprising a hollow cannula and having an insertion needle arranged there through, in which shielding means is incorporated providing a user with a high degree of protection against injury from unintended needle prick during operation and handling of the device yet providing ease of use as well as allowing the device to be manufactured in a simple and cost effective manner.

The present invention is based on the realisation that an infusion device of the above type having an insertion needle arranged through a cannula can be provided with a fully integrated needle shield by forming the needle with an integrated shield which is capable of both covering the cannula with the needle inserted there through prior to use, as well as covering the needle when it is withdrawn from the cannula, yet allowing the user to insert the cannula More specifically, this functionality is achieved by providing a "bridge" between the hub portion of the insertion device and the shield actually covering the needle/cannula, this allowing the hitherto separately supplied components to be formed integrally with each other.

Thus, in accordance with the invention, an infusion set comprising an infusion device and an insertion (puncturing) device is provided, the infusion device having a housing comprising an opening and a soft cannula extending from the housing and being in flow communication with the opening, the soft cannula having an outer tip, an insertion device adapted to be connected to said housing, the insertion device comprising a hub and a needle mounted thereon the needle being adapted to extend through the cannula and beyond the outer tip thereof when the insertion device is connected to the housing, the needle being at the outer end adapted for facilitating puncturing, wherein a shield member is provided having an initial position in which it covers the cannula and the protruding outer tip of the needle, a retracted position allowing the cannula to be inserted, and a final position in which the shield covers the needle when the insertion device has been removed from the housing.

The final position may be identical with the initial position, or it may be different as in a preferred embodiment in which the needle is bend when the shield member and the hub is locked together, whereby the bend needle provides a biasing effect between cooperating locking means on the shield part and the handle part, and whereby the bend needle closely abuts on the shield to ensure that unintended contact with the needle is avoided.

In a preferred embodiment the shield member is in the form of a single cover member extending generally along the axis of the cannula/needle, and being pivotally connected to the hub allowing it to be pivoted between its different positions. The pivoting action may be provided by a "traditional" hinge or by any flexible arrangement allowing the shield member to pivot or deflect relative to the hub. The shield member may be arranged to pivot corresponding to any desired axis, e.g. parallelly with or perpendicular to the skin surface in a situation of use.

Preferably the different positions are predefined, the housing and/or insertion device comprising mating coupling means so as to allow the shield member to lock into its initial, its retracted respectively its final position. Indeed, the mating coupling means for the initial and for the retracted positions should be adapted for releasably securing the shield in the respective positions, whereas the mating coupling means for locking the shield to the hub preferably are non-releasable to prevent reuse of the needle or inadvertent release of the shield. In case the different positions are not predefined, there may be an indefinite number of equivalent positions for each of the "functional" positions; however, the term "position" when used in the present context covers any such plurality of functionally equivalent positions.

In a preferred embodiment the housing comprises a resilient self-sealing septum mounted generally at a proximal end of the cannula for normally closing the proximal end thereof. The infusion needle being mounted there through in its initial coupled position.

In a further preferred embodiment the housing comprises a cavity having an inlet and an outlet, the outlet being in fluid communication with the cannula, the inlet being adapted for receiving the insertion needle and preferably comprises a resilient self-sealing septum as described above. The cavity may be provided with one or more additional openings providing access thereto, each opening being closed by a self-sealing septum or any other suitable closure means for sealing the opening when not in use. Indeed, in a simple configuration, the opening may be formed by the proximal end of the cannula.

All of the above features are desirably provided in an infusion set constructed from relatively simple and preferably disposable components which can be manufactured in a cost-efficient manner from medical grade plastic or the like, the needle itself preferably being made from stainless steal.

BRIEF DESCRIPTION OF THE DRAWINGS

In the following the invention will be further described with references to the drawings, wherein

FIG. 4A shows a three-dimensional representation of the infusion set of FIG. 1 with a shield member in a retracted position, FIG. 4B shows the infusion set of FIG. 4A in a side view.

DESCRIPTION OF THE PREFERRED EMBODIMENTS

Figure 1:
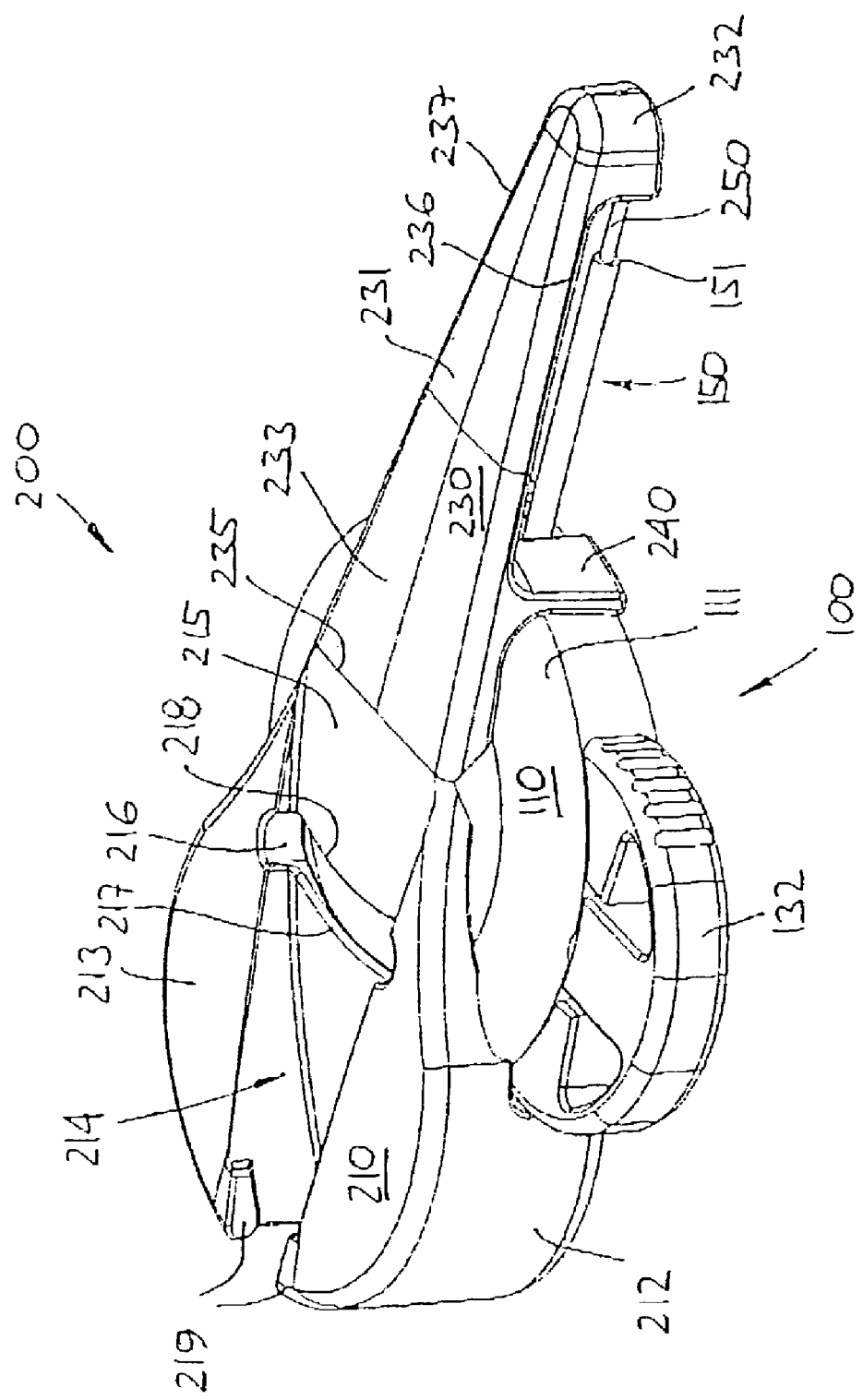
FIG. 1 shows a three-dimensional representation of an infusion set in an initial position comprising an infusion device and an insertion device in accordance with the invention.

FIG. 1 shows a preferred embodiment of the invention comprising two individual components, an infusion device 100 comprising a housing 110 and a cannula 150, and an insertion device 200 releasably coupled thereto and comprising a hub 210 and a hollow needle 250 mounted thereon, the needle being adapted to extend through the cannula and beyond the outer tip thereof when the insertion device as shown is connected to the housing, the insertion device further comprising a shield member 230 for shielding the tip of the needle. In the shown embodiment the housing comprises a cap 132 arranged in an inlet opening in the housing (to be explained in greater detail below).

The housing 110 generally has a disc-formed, circular configuration (see FIGS. 2A and 2B) defining an upper surface 111, a lower surface 112 defining a general plane for the housing as well as for the infusion set in general, a front end and a rear end, and has a central bore formed there through, the bore having a rear portion forming a cavity 115 with an opening 113 and a front portion 116 of reduced diameter. In the following these orientations will generally be used for all components and structures.

The cannula 150 comprises a straight tubular main portion 152 forming the cannula per se and having an outer tip 151 with a distal opening, and a rear portion 153 adapted to be sealingly received and mounted coaxially in the front-most portion of the bore, thereby defining an outlet from the cavity. In the rear-most portion of the cavity a resilient self-sealing septum 120 is mounted generally axially in respect of the cannula and defining an inlet for the cavity, this allowing an infusion needle to be mounted through the septum and out through the cannula. As appears, the cannula and the central bore are arranged slightly inclined with respect to the general plane of the housing, this for facilitating mounting of the infusion device on the skin surface of a user.

In the shown embodiment the housing comprises a further bore 130 in communication with the central bore and arranged perpendicularly thereto, the further bore comprising a further resilient self-sealing septum 131 defining a further inlet for the cavity, the septum being protected by a releasably mounted semi-circular cap 132, however, in order to allow a standard tube connector to be connected, the septum may be dispensed with. Optionally the housing may be provided with a peripheral cover member 118 to improve grip and appearance.

The hub 210 comprises a mounting portion 211 to which the needle 250 is fixedly mounted, two laterally arranged handle portions 212, 213 providing gripping surfaces for handling the device, an upwardly open groove 214 being defined therebetween and extending coaxially with the needle, and a forwardly protruding "bridge" portion 215 extending as a continuation of the groove. As appears, a transverse slot or opening 216 having front and rear edges 217, 218 is provided in the bridge portion as well as coupling means 219 is associated with groove, the importance of which will be described in detail below.

The shield member comprises a generally flat roof-like cover portion 231 having lateral edges 236, 237 and a rounded nose portion 232 at the distal end thereof adapted to substantially surround the pointed needle tip 251, and a rearwardly protruding "bridge" portion 233 pivotably attached to the bridge portion of the hub, thereby defining a hinge 235 which in the shown embodiment is in the form of a film-hinge. As appears, the bridge portions span across the upper surface of the housing thereby connecting the hub with the shield member. Indeed, functionally the bridge may be formed as a single portion, the hinge being arranged corresponding to a rear or front portion of the housing, or it may be provided by lateral members arranged along the sides of the housing, or in any other suitable way.

Figure 3:
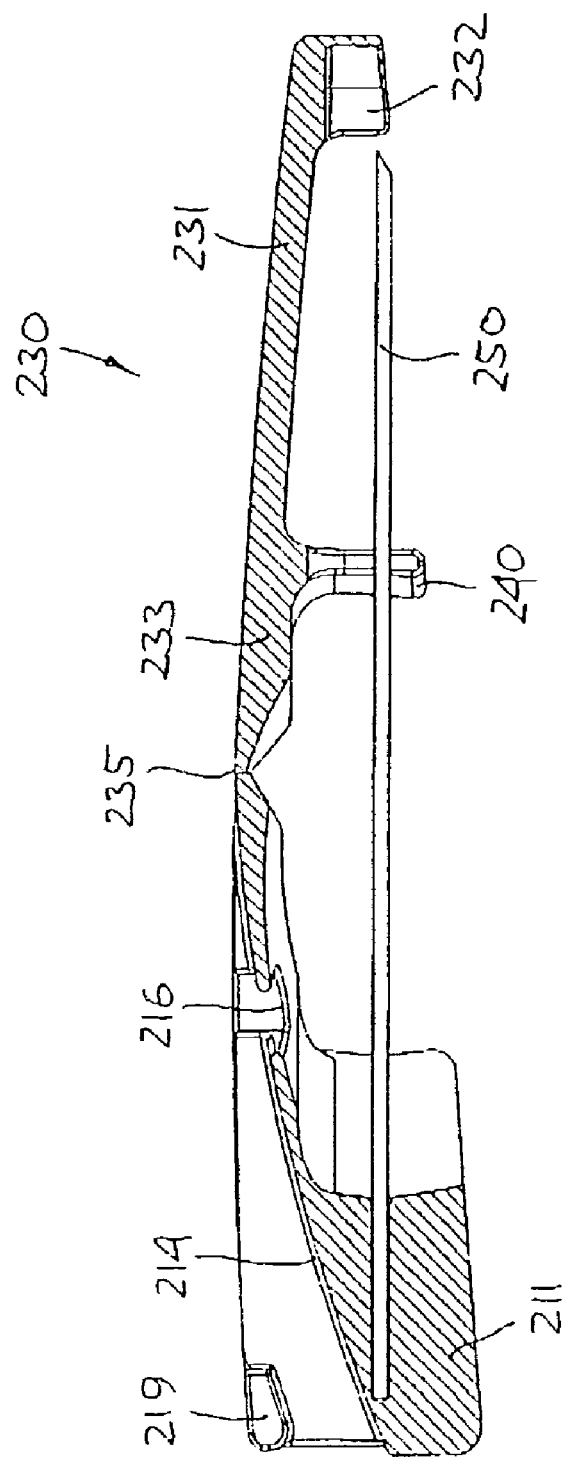
FIG. 3 shows a longitudinal cross-sectional view of the insertion device shown in FIG. 1.

Protruding downwardly from the proximal portion of the cover are arranged coupling arms 240 formed with coupling means adapted to engage corresponding mating coupling means on the housing. The coupling means may be in the form of distal hook members arranged on the arms gripping edge portions on the housing, or the arms may be slightly inwardly curved as shown. In FIG. 3 the insertion device is shown detached from the housing.

Figure 2A:
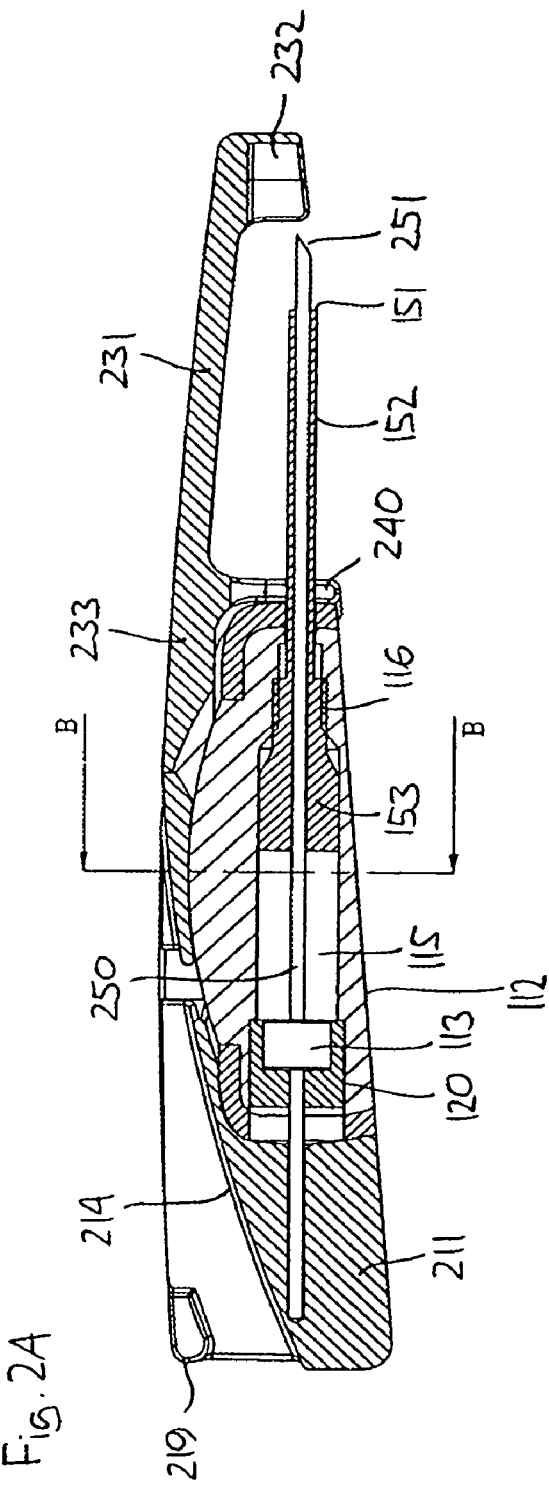
FIG. 2A shows a longitudinal cross-sectional view of the set shown in FIG. 1.
Figure 2B:
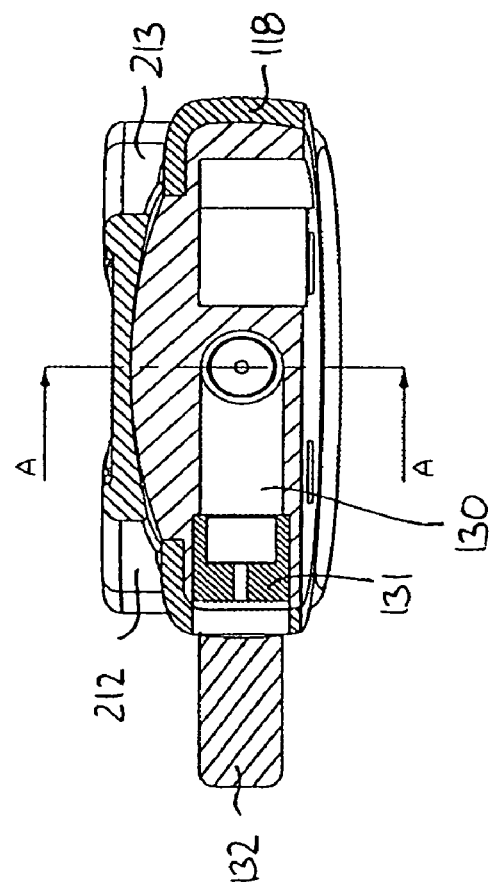
FIG. 2B shows a transverse cross-sectional view of the set shown in FIG. 1.

In FIGS. 1, 2A and 2B the infusion set is shown in its initial state as supplied to the user, i.e, with the needle mounted through the cavity and with the pointed tip protruding from the distal opening of the cannula, and with the shield member arranged generally coaxially with the cannula/needle, the nose portion 232 substantially surrounding the needle tip. Due to the coupling arms 240 the shield member as well as the insertion device as such is locked in piece to the housing Next, use of the device in accordance with the invention will be described. In order to insert the cannula with the needle arranged there through, the shield member 230 is pivoted upwardly and backwardly approximately 180 degrees as shown in FIGS. 4A and 4B, thereby positioning the shield member in the retracted position allowing the cannula to be inserted. In the shown embodiment the shield member is positioned and locked in place in the groove 214 formed in the hub, the coupling means 219 associated with groove gripping the lateral edges 236, 237 of the shield thereby holding it releasably in place, this providing for improved handling during the insertion procedures.

In the shown embodiment no special locking means is provided between the hub and the housing, the components being coupled to each by the frictional engagement between the needle and the septum respectively the inside of the cannula. In case the resistance to penetration by the needle is high, the user will grip the infusion set to gently press the components together corresponding to the longitudinal axis of the cannula. If deemed necessary, a releasable locking means may be provided between the hub and the housing.

In order to indicate that the needle tip has been positioned in a blood vessel, the proximal end of the needle may be in fluid communication with a ventilated so-called flash chamber (not shown) which is adapted to be filled with blood a transparent window allowing this to be observed by the user. Indeed, in case the cannula is intended for being placed at a selected subcutaneous site, such a chamber would not be relevant.

When the needle tip has been positioned properly, e.g. at a selected subcutaneous site or in a blood vessel, the insertion device and thus the needle is retracted from the cannula and the housing. The lower surface of the housing may be provided with an adhesive allowing it to be attached to the skin surface of the user, or it may be held in place by additional adhesive means. After this, a fluid source may be connected to any of the fluid inlets to the cavity for supplying a fluid out through the cannula.

Figure 5A:
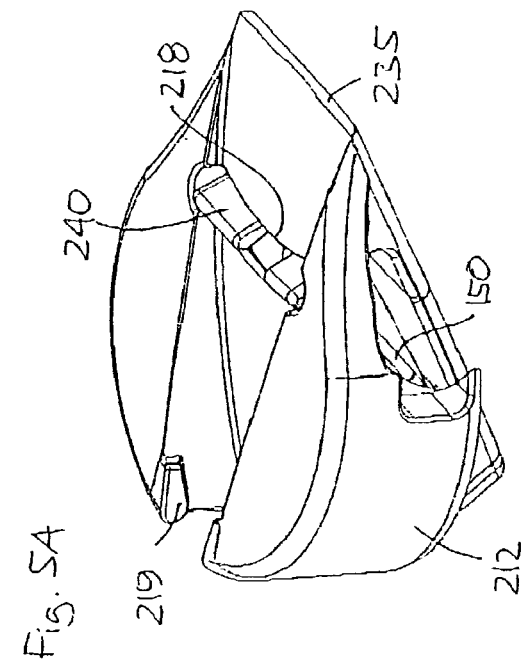
FIG. 5A shows a three-dimensional representation of the insertion device of FIG. 3 with the shield member in a final position.
Figure 5C:
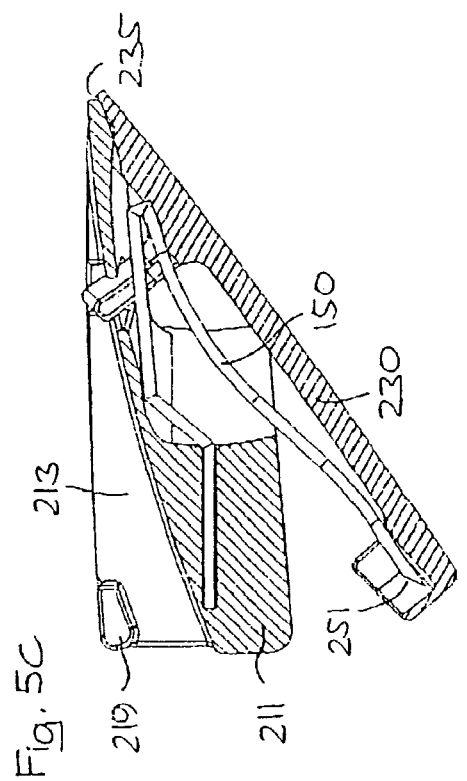
FIG. 5C shows a longitudinal cross-sectional view of the insertion device of FIG. 5A.
Figure 5B:
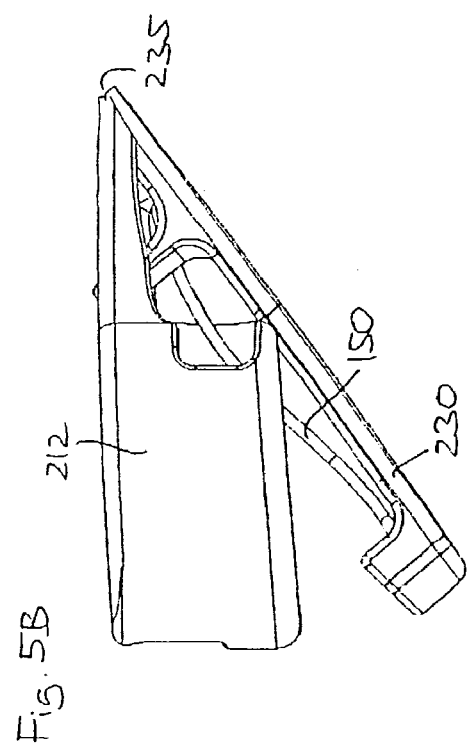
FIG. 5B shows the insertion device of FIG. 5A in a side view.

When the insertion device has been withdrawn from the infusion device, the shield member is disengaged from the groove and pivoted to a final position at least covering the needle. In the shown embodiment the shield member is pivoted further downwardly and subsequently upwardly until engagement with a lower surface of the hub thereby bending the needle as shown in FIGS. 5A–5C As appears, the shield member is thereby pivoted approximately 315 degrees (⅞ of a full turn) from the retracted position to the final position. In order to properly secure the shield member in its final position, the coupling arms 240 are formed with coupling means adapted to engage corresponding mating coupling means associated with the slot 216 when placed there through. The coupling means may be in the form of distal hook members on the arms adapted to engage a sharp edge on the front edge 218, or the arms may be gripped by both of the front and rear edge 217, 218. As appears, by this arrangement the coupling means on the shield member may be used with corresponding coupling means on both the housing and the hub. To prevent inadvertent release of the shield, the coupling means between the shield member and the hub should to a high degree be "non-releasable", i.e. to function as locking means.

As the needle is bend when the shield member and the hub is locked together, the bend needle provides a biasing effect between the locking means and assures that the bend needle closely abuts on the shield to further ensure that unintended contact with the needle is avoided.

Figure 6:
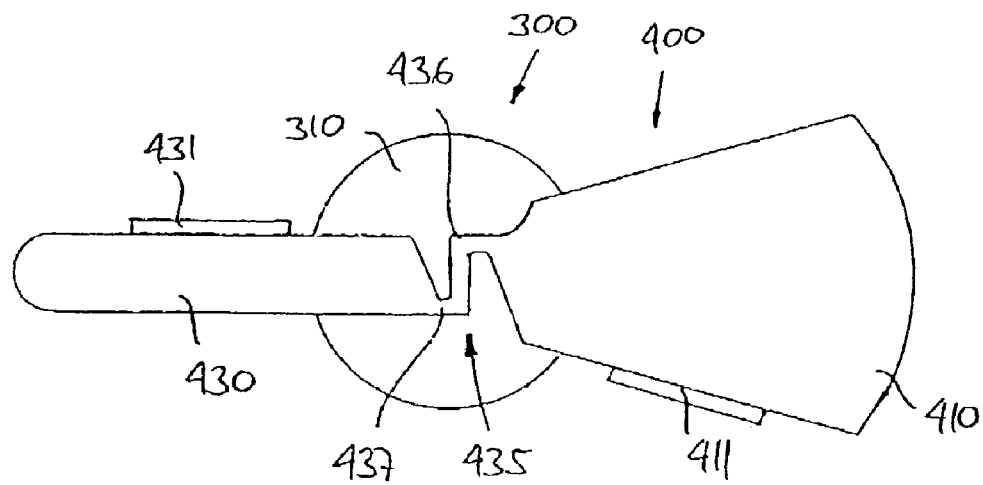
FIG. 6 shows a schematic representation of a further embodiment an infusion set in an initial position.
Figure 7:
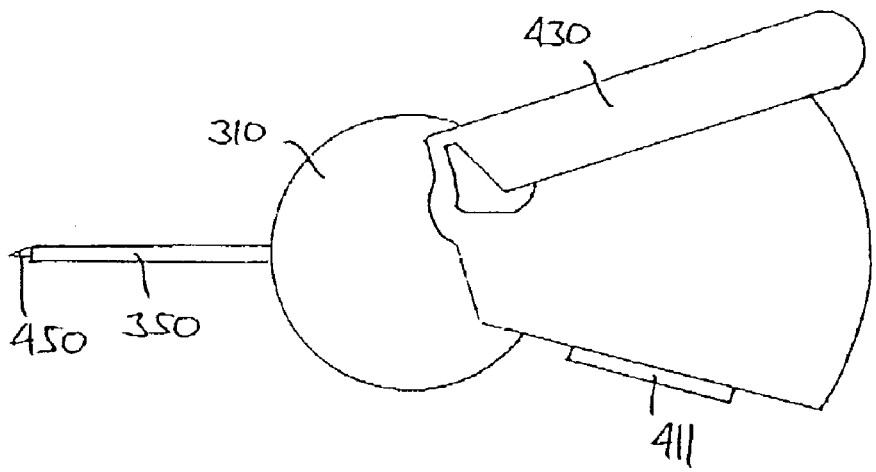
FIG. 7 shows the infusion set of FIG. 6 with the shield member in a retracted position.
Figure 8:
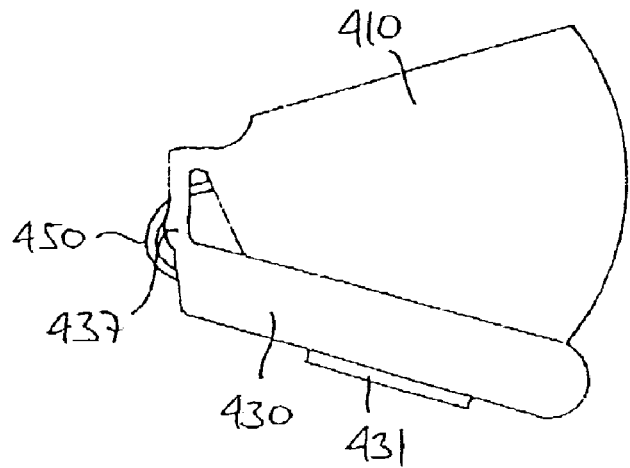
FIG. 8 shows the insertion device of FIG. 6 with the shield member in a final position

With reference to FIGS. 6–8 a second preferred embodiment will be described, the second embodiment generally having a configuration corresponding to the first embodiment More specifically, FIG. 6 shows an infusion set comprising two individual components, an infusion device 300 comprising a disc formed housing 310 (defining a general plane for the infusion set) and a cannula 350, and an insertion device 400 releasably coupled thereto and comprising a hub 410 and a hollow needle 450 mounted thereon, the needle being adapted to extend through the cannula and beyond the outer tip thereof when the insertion device as shown is connected to the housing, the insertion device further comprising a shield member 430 for shielding the tip of the needle. Whereas the first embodiment was provided with a hinge 235 allowing the shield member to pivot corresponding to a "well-defined" axis parallel with the general plane of the infusion device, the second embodiment is provided with a flexible hinge member 435 in the form of a zigzag portion allowing the shield member to deflect to either side, i.e. in the general plane of the infusion device. Mating coupling means are provided on the shield member respectively the hub for releasably locking the shield member in the retracted position, respectively for locking the shield member in the final position in which the shield covers the needle when the insertion device has been removed from the housing.

Next, use of the device corresponding to the second embodiment will be described. In order to insert the cannula with the needle arranged there through, the shield member 430 is pivoted backwardly towards the hub 410 approximately 160 degrees as shown in FIG. 7, thereby positioning the shield member in the retracted position allowing the cannula to be inserted, see FIG. 7. As appears, the shield member pivots corresponding to a first hinge member 436 of the zigzag portion. As shown, the shield member is positioned and locked in place along a side portion of the hub by a flange 431 being gripped by a corresponding slot (not shown) in the hub thereby holding it releasably in place, this providing for improved handling during the insertion procedures.

After the cannula has been placed, the insertion device is withdrawn from the infusion device and the shield member is disengaged from the hub and "pivoted" to a final position covering the needle, see FIG. 8. As appears, the shield member first pivots corresponding to the first hinge member 436 of the zigzag portion and thereafter corresponding to a second hinge member 437, whereby the shield member is "pivoted" approximately ⅞ of a full turn from the retracted position to the final position. Indeed, in a factual situation of use, both hinge members will participate when the shield member is pivoted to either side. In order to properly secure the shield member in its final position, the hub is formed with coupling means 411 adapted to engage corresponding mating coupling means (not shown) on the shield member. To prevent inadvertent release of the shield, the coupling means between the shield member and the hub should to a high degree be "non-releasable", i.e. to function as locking means As in the first embodiment, the needle is bend when the shield member and the hub is locked together, the bend needle providing a biasing effect between the locking means.

While the present invention has been described in connection with the preferred embodiment shown in the various figures, it is to be understood that other similar embodiments may be used or modifications and additions may be made to the described embodiment for performing the same function of the present invention without deviating there from. For example, the shield may be provided by two or more members connected to each other, just as the means allowing the shield member to move between the different positions relative to the hub may be provided by e.g. a telescoping arrangement instead of one or more hinges.

Therefore, the present invention should not be limited to any single embodiment, but rather construed in accordance with the appended claims.

The invention claimed is:

1. An infusion set comprising:
an infusion device having a housing comprising an opening and a soft cannula extending from the housing and being in flow communication with the opening, the soft cannula having an outer tip,
an insertion device adapted to be releasably connected to the housing, the insertion device comprising a hub and a needle mounted thereon, the needle being adapted to extend through the opening and beyond the outer tip of the cannula when the insertion device is connected to the housing, the needle being at the outer end adapted for facilitating puncturing,
wherein the insertion device further comprises a shield member pivotally connected to said hub, and having at least one first position in which it covers the cannula and the protruding outer tip of the needle when the insertion device is connected to the housing, at least one second position allowing the cannula to be inserted into the body of a patient when the insertion device is connected to the housing, said shield member being movable upon removal of said insertion device from said housing to at least one third position in which said shield member covers the needle and the outer tip thereof.

2. An infusion set as defined in claim 1, wherein the hub and the shield member in combination provides a bridging means spanning the housing from a rear to a front portion thereof.

3. An infusion set as defined in claim 1, wherein the housing comprises a cavity having a rear end with an opening, and an opposed front end in fluid communication with the cannula, the needle being mounted through the opening and out through the cannula, the opening preferably comprising a self-sealing penetratable septum allowing the needle to be mounted there through.

4. An infusion set as defined in claim 1, wherein the housing has a generally flat configuration with a lower surface adapted to engage a skin surface of a user and an opposed upper surface, the insertion device comprising a bridge portion spanning the upper surface, the bridge portion comprising a hinge member allowing the shield member to pivot relative to the hub.

5. An infusion set as defined in claim 1, wherein the housing has a lower surface adapted to engage a skin surface of a user and defining a general plane for the infusion set, the shield member being arranged to pivot relative to the hub corresponding to an axis in parallel with or perpendicular to the general plane.

6. An infusion set comprising:
an infusion device having a housing comprising an opening and a soft cannula extending from the housing and being in flow communication with the opening, the soft cannula having an outer tip,
an insertion device adapted to be releasably connected to the housing, the insertion device comprising a hub and a needle mounted thereon, the needle being adapted to extend through the opening and beyond the outer tip of the cannula when the insertion device is connected to the housing, the needle being at the outer end adapted for facilitating puncturing,
wherein the insertion device further comprises a shield member pivotally connected to said hub, and having a position in which it covers the cannula and the protruding outer tip of the needle when the insertion device is connected to the housing, a position allowing the cannula to be inserted into the body of a patient when the insertion device is connected to the housing, said shield member being movable upon removal of said insertion device from said housing to a position in which said shield member covers the needle and the outer tip thereof, wherein mating coupling means are provided on the shield member and the housing for releasably locking the shield member in an initial position in which it covers the cannula and the protruding outer tip of the needle when the insertion device is connected to the housing.

7. An infusion set comprising:

an infusion device having a housing comprising an opening and a soft cannula extending from the housing and being in flow communication with the opening, the soft cannula having an outer tip, an insertion device adapted to be releasably connected to the housing, the insertion device comprising a hub and a needle mounted thereon, the needle being adapted to extend through the opening and beyond the outer tip of the cannula when the insertion device is connected to the housing, the needle being at the outer end adapted for facilitating puncturing, wherein the insertion device further comprises a shield member pivotally connected to said hub, and having a position in which it covers the cannula and the protruding outer tip of the needle when the insertion device is connected to the housing, a position allowing the cannula to be inserted into the body of a patient when the insertion device is connected to the housing, said shield member being movable upon removal of said insertion device from said housing to a position in which said shield member covers the needle and the outer tip thereof, wherein mating coupling means are provided on the shield member and the hub for locking said shield member in said position in which the shield member covers the needle when the insertion device has been removed from the housing.

8. An infusion set as defined in claim 7, wherein the needle is bent when the shield member and the hub are locked together, whereby the bent needle provides a biasing effect between cooperating locking means on the shield part and the handle part, and whereby the bent needle closely abuts on the shield.

* * * * *